(12) United States Patent
Davis et al.

(10) Patent No.: US 6,681,135 B1
(45) Date of Patent: Jan. 20, 2004

(54) SYSTEM AND METHOD FOR EMPLOYING TEMPERATURE MEASUREMENTS TO CONTROL THE OPERATION OF AN IMPLANTABLE MEDICAL DEVICE

(75) Inventors: Timothy J. Davis, Coon Rapids, MN (US); James D. Reinke, Maple Grove, MN (US); David W. Graden, Shoreview, MN (US); John D. Wahlstrand, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 105 days.

(21) Appl. No.: 09/725,329

(22) Filed: Nov. 22, 2000

Related U.S. Application Data

(60) Provisional application No. 60/244,264, filed on Oct. 30, 2000.

(51) Int. Cl.[7] ................................................. A61N 1/18
(52) U.S. Cl. ........................................... 607/21; 607/30
(58) Field of Search ................................. 607/18–22, 25, 607/116, 127, 1, 2, 4, 6, 7, 30, 32; 600/323, 300, 487, 485, 375, 377, 500, 513; 606/78; 128/898, 903, 904

(56) References Cited

U.S. PATENT DOCUMENTS

| | | | |
|---|---|---|---|
| 4,230,120 A | 10/1980 | McDonald | |
| 4,259,639 A | 3/1981 | Renirie | |
| 4,276,883 A | 7/1981 | McDonald et al. | |
| 4,290,429 A | 9/1981 | Blaser | |
| 4,313,079 A | 1/1982 | Lee | |
| 4,345,603 A | 8/1982 | Schulman | |
| 4,448,197 A | 5/1984 | Nappholz et al. | |
| 4,782,836 A | 11/1988 | Alt | |
| 4,905,697 A | 3/1990 | Heggs et al. | |
| 4,945,909 A | 8/1990 | Fearnot et al. | |
| 4,958,632 A | 9/1990 | Duggan | |
| 5,014,704 A | * 5/1991 | Alt | 607/21 |
| 5,052,388 A | 10/1991 | Sivula et al. | |
| 5,089,019 A | 2/1992 | Grandjean | |
| 5,336,244 A | 8/1994 | Weijand | |
| 5,350,407 A | 9/1994 | McClure et al. | |
| 5,387,228 A | 2/1995 | Shelton | |
| 5,402,070 A | 3/1995 | Shelton et al. | |
| 5,423,869 A | * 6/1995 | Poore et al. | 607/18 |
| 5,456,692 A | 10/1995 | Smith, Jr. et al. | |
| 5,496,312 A | 3/1996 | Klicek | |
| 5,509,424 A | 4/1996 | Al-Ali | |
| 5,534,018 A | 7/1996 | Wahlstrand et al. | |
| 5,562,711 A | 10/1996 | Yerich et al. | |
| 5,596,995 A | 1/1997 | Sherman et al. | |
| 5,707,369 A | 1/1998 | Vaitekunas et al. | |
| 5,713,933 A | 2/1998 | Condie et al. | |
| 5,730,125 A | * 3/1998 | Prutchi et al. | 600/323 |
| 5,743,903 A | 4/1998 | Stern et al. | |
| 5,810,802 A | 9/1998 | Panescu et al. | |
| 5,814,087 A | 9/1998 | Renirie | |
| 5,861,013 A | 1/1999 | Peck et al. | |
| 5,897,576 A | 4/1999 | Olson et al. | |
| 5,906,614 A | 5/1999 | Stern et al. | |

* cited by examiner

Primary Examiner—Tu Ba Hoang
(74) Attorney, Agent, or Firm—Girma Wolde-Michael; Michael C. Soldner

(57) ABSTRACT

A medical implantable device that includes a temperature sensor circuit and a control circuit coupled to the temperature sensor circuit to control non-therapy operation of the medical implantable device in response to temperature measurements obtained by the temperature sensor circuit.

28 Claims, 16 Drawing Sheets

SYSTEM AND METHOD FOR EMPLOYING TEMPERATURE MEASUREMENTS TO CONTROL THE OPERATION OF AN IMPLANTABLE MEDICAL DEVICE

RELATED APPLICATIONS

This application claims priority to provisional application Ser. No. 60/244,264, filed Oct. 30, 2000, entitled "Device and Method for Ablating Ostia of Pulmonary Veins and Other Lumens" and which is incorporated herein by reference in its entirety.

FIELD OF THE INVENTION

This invention relates generally to monitoring the internal temperature of an electronic device; and, more particularly, relates to a system and method for detecting and recording the temperature of an implantable medical device, such as a pacemaker or defibrillator, and using the temperature information to control the operation of the implantable medical device.

BACKGROUND OF THE INVENTION

Temperature measurements have been utilized in the past in conjunction with the control and operation of surgical medical tools. Such measurements are commonly used to determine when a treatment using heating energy is completed. For example, surgical tools are available to deliver energy to tissue at a point of incision to cause coagulation and prevent excessive bleeding. Such surgical tools may use temperature measurements taken from the treated tissue to determine when coagulation has been completed. A system of this nature is disclosed by U.S. Pat. No. 5,707,369 to Vaitekunas et al., which describes the use of temperature to determine when coagulation of tissue has occurred to a desired degree. Another similar example is provided by U.S. Pat. No. 5,496,312 to Klicek, which describes use of temperature measurements to regulate power supplied by a electrosurgical generator used to perform tissue desiccation. Tissue ablation systems also commonly use temperature measurements of adjacent tissue to control the amount of delivered ablation energy. Examples of these types of systems are provided by U.S. Pat. Nos. 5,743,903 and 5,906,614, both to Stern et al., and U.S. Pat. No. 5,810,802 to Panescu et al.

In addition to measuring temperature of adjacent body temperature, some medical systems use the temperature of internal circuitry to adjust system operation and performance. U.S. Pat. No. 5,897,576 to Olson et al. discloses an external defibrillation system that senses the temperature inside the power supply case of the device, and uses these measurements to adjust the operating parameters of the system, including capacitor charge time.

Implantable Medical Devices (IMDs) have also been provided that utilize temperature measurements to adjust therapy delivery. U.S. Pat. No. 4,905,697 to Heggs et al. describes a system that uses temperature sensed within the right ventricle of the heart to determine when a patient is exercising so that pacing rate may be elevated. Another similar system is disclosed in U.S. Pat. No. 4,782,836 to Alt et al. U.S. Pat. No. 5,814,087 to Renirie discloses a system that uses a drop in blood temperature to detect the onset of sleep so that pacing rate may be adjusted accordingly. Other pacemaker systems have been provided that use body temperature to perform capture detection. Such a system is disclosed in U.S. Pat. No. 5,336,244 to Weijand. Yet another example of the use of temperature within an IMD is provided by U.S. Pat. No. 5,089,019 to Grandjean, which discloses a system that uses intramuscular temperature to monitor performance of an implantable skeletal muscle powered cardiac assist system.

In addition to using temperature measurements for the purposes discussed in the foregoing paragraphs, a need exists to utilize temperature to regulate and control the system functions of an IMD that are not directly related to therapy delivery. One case in which temperature may be utilized in such a manner involves what is known as an Elective Replacement Indicator (ERI). An ERI is an indicator that is asserted when the battery power of an IMD has reached a predetermined low level. Upon assertion of this indicator, a battery replacement procedure is typically scheduled. This indicator may also be used to disable non-essential circuits so that overall power consumption decreases and battery power is conserved. The assertion of the ERI may further cause a pacing device to revert to a nominal pacing mode to further conserve power. One problem with the ERI is that sometimes this indicator may be erroneously set. This may occur prior to implant when an IMD is subjected to cold temperatures for a period of time. Cold temperatures cause the voltage of the IMD battery to drop. This initial voltage drop, or the subsequent voltage increase that occurs when the IMD returns to a warmer temperature, may cause the low-battery condition to be incorrectly detected. This, in turn, results in a latching of the ERI condition. In some circumstances, this may place the IMD in a low-battery state that can only be corrected using a manual override. To prevent this erroneous detection of a low-power condition, it is desirable to disable the ERI when the IMD reaches a predetermined low temperature.

Another situation in which temperature measurements may be used to control the logic functions of an IMD relates to a high-temperature quality control process known as "burn-in". The burn-in process is used during manufacturing to stress the electrical components of the pacemaker by subjecting them to high temperatures and high operating voltages. The components that fail during burn-in are not used in products. Although most circuits are required to function at a burn-in temperature of 135° C., some circuits to such as CMOS bias generator mirror structures experience a significant shift in operating point that affects testing results. Additionally, some analog circuits must be provided with an increased current to operate properly at elevated temperatures. It is desirable to sense burn-in temperatures so that functions vulnerable to the high stress factors can be automatically disabled or appropriately compensated, and burn-in test results will not be erroneously affected by these circuits.

Yet another need for using temperature to control IMD operation involves the disabling of pacing and other functions of the IMD during the shelf-life of the device. This is useful for conserving battery power until the time of implant. This disabling function could be triggered, for example, by determining that the temperature of the IMD is not being maintained at a temperature that generally coincides with body temperature. Similarly, the detection of a temperature approximating body temperature could be used by the IMD to confirm the occurrence of implantation. These measurements could be used either alone, or in conjunction with other detection mechanisms such as body activity or impedance measurements taken between electrodes, to detect implantation.

Other uses of IMD temperature involve obtaining temperature measurements to control other treatment-related functions of the medical device. For example, the IMD temperature may be recorded to detect periods of extended exercise. Such extended periods of exercise will generally result in raising the internal body temperature. Upon detection of extended periods of exercise, the decay time constants can be adjusted. For example, following a prolonged period of exercise, it may be desirable to increase the time over which an elevated pacing rate is slowed to a normal pacing rate. It may also be useful to use temperature to set upper and lower rate limits. For example, after implantation is detected, a temperature above body temperature that is sustained for an extended period may be used to limit the upper pacing rate. Similarly, following implant, if a temperature below body temperature is detected for a substantial period to time as may occur during medical procedures such as an ice bath, the lower pacing rate may be limited so that the pacing rate does not drop too low.

Temperature measurements may also be used to compensate logical functions that are temperature sensitive. For example, some circuits such as Analog-to-Digital Converters require a reference voltage to operate properly. However, the reference voltage may drift with temperature changes, causing circuit operation that also varies with the temperature. A voltage compensation circuit may be provided to compensate for reference variations that are the result of temperature changes. Such a device may be programmably re-calibrated with data that reflects a current temperature, thereby making the circuit operation relatively temperature independent.

It is thus an object of the invention to provide an integrated temperature sensing circuit in an IMD to control system functions. Such control may prevent the erroneous assertion of an ERI indicator during exposure to cold temperatures, while allowing for correct burn-in results during high-temperature operations. This control may further provide a verification of implantation, or may be used to monitor a patient's internal temperature for immediate diagnostic purposes and to establish long-term trends in patient health. Temperature measurements may provide an indication of the duration of exercise so that decay constants may be adjusted, and detect external conditions such as medical procedures that require change of system functions. Temperature changes may also cause the recalibration of certain circuit functions so that circuit operation can be made temperature independent.

SUMMARY OF THE INVENTION

The current invention is an Implantable Medical Device (IMD) having a temperature sensor to sense the temperature of the IMD, and to utilize the temperature measurements to control at least one system function provided by the IMD. Generally, this control relates to determining or controlling the state of the IMD. In one embodiment, temperature measurements are utilized to prevent the erroneous latching of a low-power warning indication that may be falsely triggered if an IMD is subjected to cold conditions during storage prior to implant. In another embodiment, the temperature measurements are used to detect the occurrence of a burn-in process that is used to stress IMDs during testing. If burn-in conditions are detected, it may be desirable to automatically disable certain ones of the analog circuits. This places certain circuits in a known state, and may further compensate voltage and current levels for some circuits so that the burn-in tests can be completed normally without the testing system requiring manual intervention. Another aspect of the invention uses temperature readings to allow temperature-sensitive circuits to be programmably recalibrated if temperature changes occur. Yet another embodiment of the invention uses temperature measurements to confirm the occurrence of implantation of a device. If implantation has not yet occurred, certain logical functions may be disabled to conserve battery power.

Other embodiments of the invention may utilize temperature measurements to monitor patient environment and activity levels. For example, extended periods of elevated temperature measurements may be used to detect prolonged periods of exercise. Such situations may prompt the extension of decay times so that pacing rates decay more gradually from an elevated rate to a resting rate following termination of the patient activity. In other situations, elevated temperatures may prompt the setting of an upper pacing rate limit. This may be desirable if the temperature increase is caused by a non-exercise condition such as the exposure to an X-ray source. This type of state could be detected by using measurements from both a temperature sensor and an activity sensor, for example. Yet other situations involving an extended period of colder-than-normal temperatures detected following implant may prompt the setting of a lower pacing rate limit so that pacing rates do not drop excessively during treatments such as ice baths. Temperature measurements are also available to be transferred to external devices such as programmers for later diagnostic purposes.

In one embodiment of the invention, the temperature sensor of the IMD comprises two mismatched transistors connected to a current supply with the transistors having substantially the same collector current. The transistors have a voltage difference between their control nodes that is proportional to the temperature of the electronic device. The mismatched transistors may be bipolar transistors having a size ratio of eight to one. The IMD may further comprise a gain circuit to programmably set the scale and resolution of the temperature sensor.

Other aspects of the invention will become apparent from the drawings and the specification.

DETAILED DESCRIPTION OF THE PREFERRED EMBODIMENTS OF THE INVENTION

A. System Environment

Figure 1:
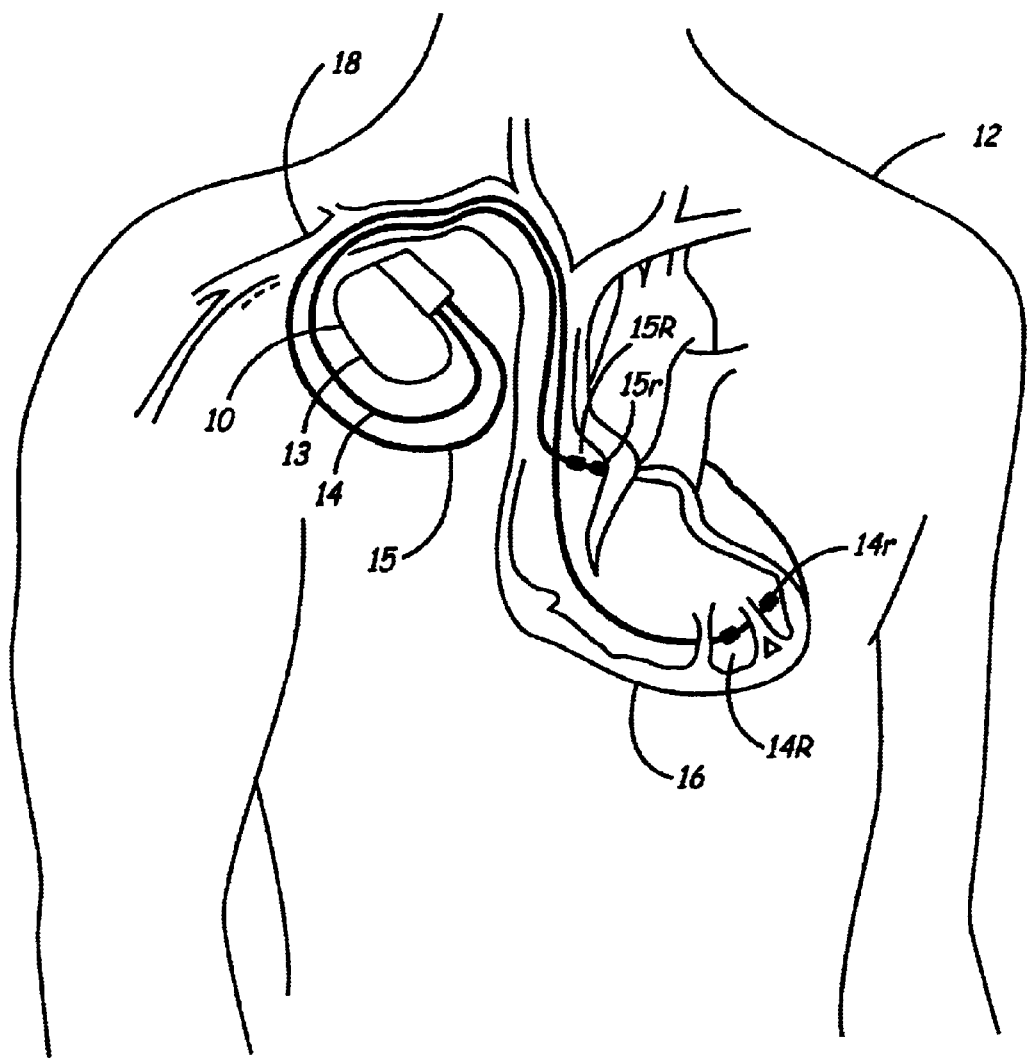
FIG. 1 is a diagram of an Implantable Medical Device and leads implanted within a patient.

FIG. 1 illustrates an Implantable Medical Device (IMD) 10 which may be a pacemaker or defibrillator implanted in a patient 12. By way of example only, the IMD 10 is illustrated as an implantable cardiac pacemaker and it is to be understood that the IMD 10 may be any electronic device having programmable electronic logic functions which are initiated or are disabled in part because of the internal temperature of the IMD 10. Moreover, the IMD need not be limited to cardiac devices., For example, the IMD may be an insulin pump or other implantable devices administering medication or biological compounds that uses temperature to control the logical functions within the device in a manner similar to that discussed herein.

The exemplary IMD 10 of FIG. 1 may have a pulse generator comprising a hermetically sealed, biologically inert outer housing or canister which may itself be conductive and thus serve as an electrode 13 in the pacemaker's pacing/sensing circuit. Disposed within the pulse generator are.electronics to monitor the condition ofthe heart, and to respond by initiating pacing pulses at a determined or increased frequency. One or more pacemaker leads 14 and 15 may be electrically coupled to the IMD 10 and extend into the patient's heart 16 through a vein 18. One or more exposed conductive ring electrodes 14R, 15R and/or tip electrodes 14T, 15T may further be located near the distal end of leads 14 and 15. The electrodes may be utilized to sense electrical cardiac depolarization signals, and/or to deliver electrical pacing pulses to the heart 16.

As is known, leads 14 and 15 may be implanted with the distal end embedded in the atrium and/or ventricle of heart 16. When used to sense cardiac signals, electrical signals are transmitted from one of these electrodes to a sense amplifier in the pulse generator. These signals are then amplified, conditioned, and digitized for further processing as required by the pacemaker's microprocessor and/or storage in digital memory of the pacemaker.

Figure 2:
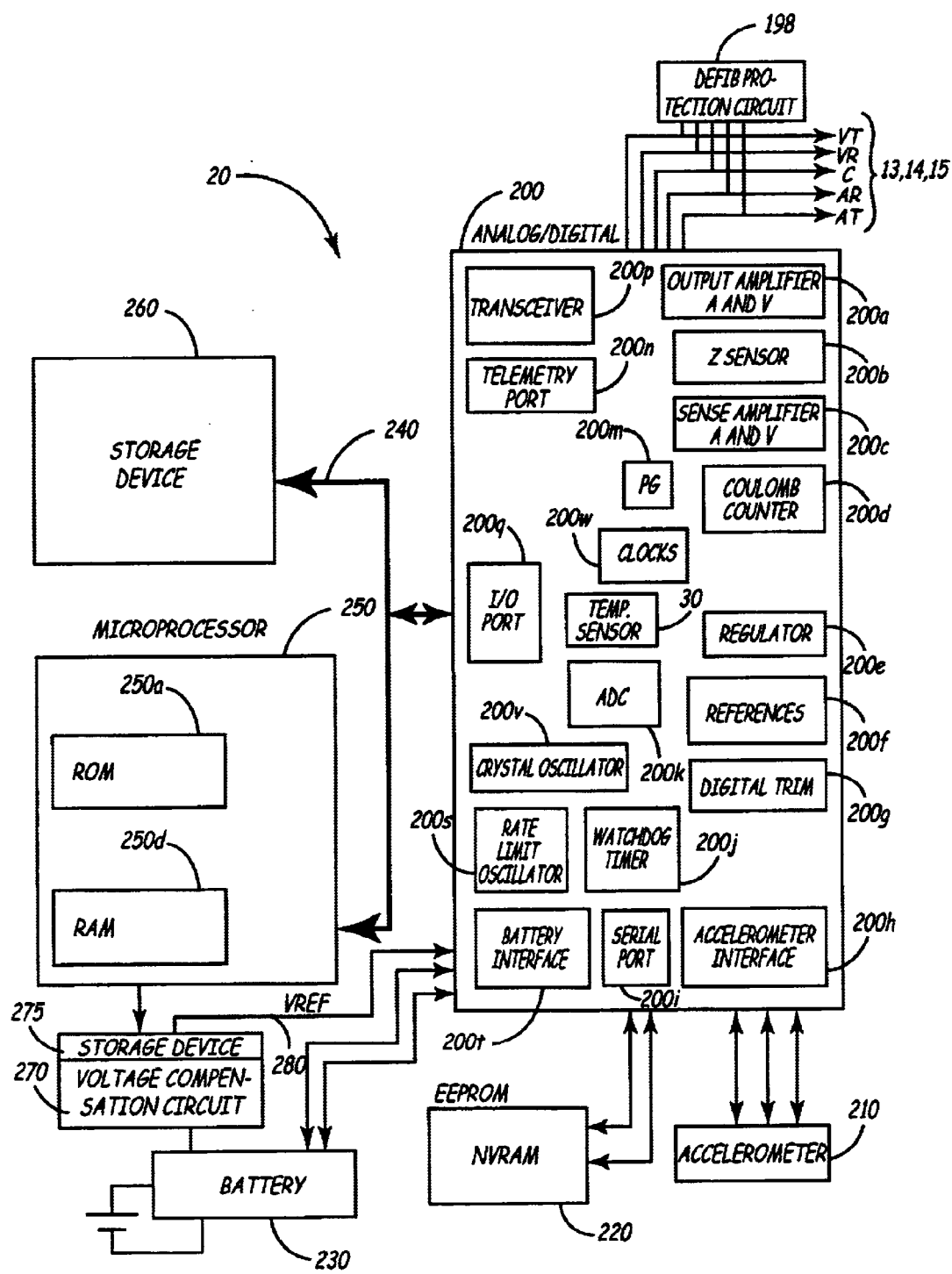
FIG. 2 is a block diagram of exemplary electronic circuitry that may be included within an implantable pulse generator.

FIG. 2 is a block diagram of exemplary electronic circuitry 20 within an IMD 10, which in the current example is a pacemaker. Block 200 comprises a plurality of analog and digital circuits and signal conditioners for various functions related to the pacemaker. Output amplifier 200a may be connected to the electrodes 13, 14, and 15, and to a defibrillation protection circuit 198 to deliver a cardioversion or defibrillation shock to a patient. Sense amplifier 200c and impedance sensor 200b may also connected to the electrodes 14 and 15 to measure electrical signals and to sense lead impedance, respectively. Coulomb counter 200d monitors the current through the battery 230. Regulator 200e and references 200f provide appropriate current and voltage values used throughout the IMD 10. Digital trim 200g receives a predetermined correction voltage from the temperature sensing circuit 30.

The IMD of FIG. 2 further includes watchdog timer 200j for monitoring the proper execution of instructions in CPU 250b of the attached microprocessor 250, and to reset some or all of the circuitry if the system enters a non-responsive state. Serial port 200i communicates with an electrically erasable programmable read only memory (EEPROM) 220 which may store key operational parameters of the pacemaker, such as reset parameters to restore functions of the pacemaker and shipping parameters. Analog-to-Digital Converter (ADC) 200k converts analog signals such as those received from electrodes 13, 14, and 15, temperature, battery voltage, and battery impedance into digital signals for processing by the microprocessor 250. Some of these signals may be storage by the IMD, or signals may be transferred to an external device such as a programmer.

Pulse Generator (PG) 200m may be provided by a counter/timer circuit or a state machine, and functions to control the rate, mode, and pacing functions of the IMD. Crystal /oscillator 200r and clocks 200w provide accurate clocking frequency for the circuitry 200 and for the delivery of pacing pulses to the patient. Rate limit oscillator 200s provides an independent back-up of the pacing rate of the pacemaker. Battery 230, preferably a lithium iodide battery, is connected to the circuitry 20 through a battery interface 200t that is also connected to the coulomb counter 200d. Transceiver 200p and telemetry port 200n are associated with communication and control of the pacemaker-unit through an external programmer as is known in the art.

Bus 240 provides for communication between the electronic circuitry 200, microprocessor 250, and storage device 260. Storage device 260 may be static or dynamic Random Access Memory (RAM), Read-Only Memory (ROM) or any combination thereof, and may be used to store instructions or data.

The exemplary IMD 20 also includes microprocessor 250 for executing instructions to control the operation of IMD. Such instructions may implement the various algorithms associated with using temperature measurements to control IMD functions in the manner to be discussed in detail below. Microprocessor 250 may include an embedded memory device such as ROM 250a and/or RAM 250d for storing instructions or data. In the illustrated embodiment, the microprocessor is shown coupled to external storage device 260 via bus 240.

Finally, IMD includes a voltage adjustment circuit 270 for providing a reference voltage on line 280. Voltage adjustment circuit includes at least one storage device 275 to receive programmable data from microprocessor 250. This data is used to adjust the reference voltage in a manner to be discussed below.

B. Exemplary Temperature Sensor for Use in an IMD

Figure 3:
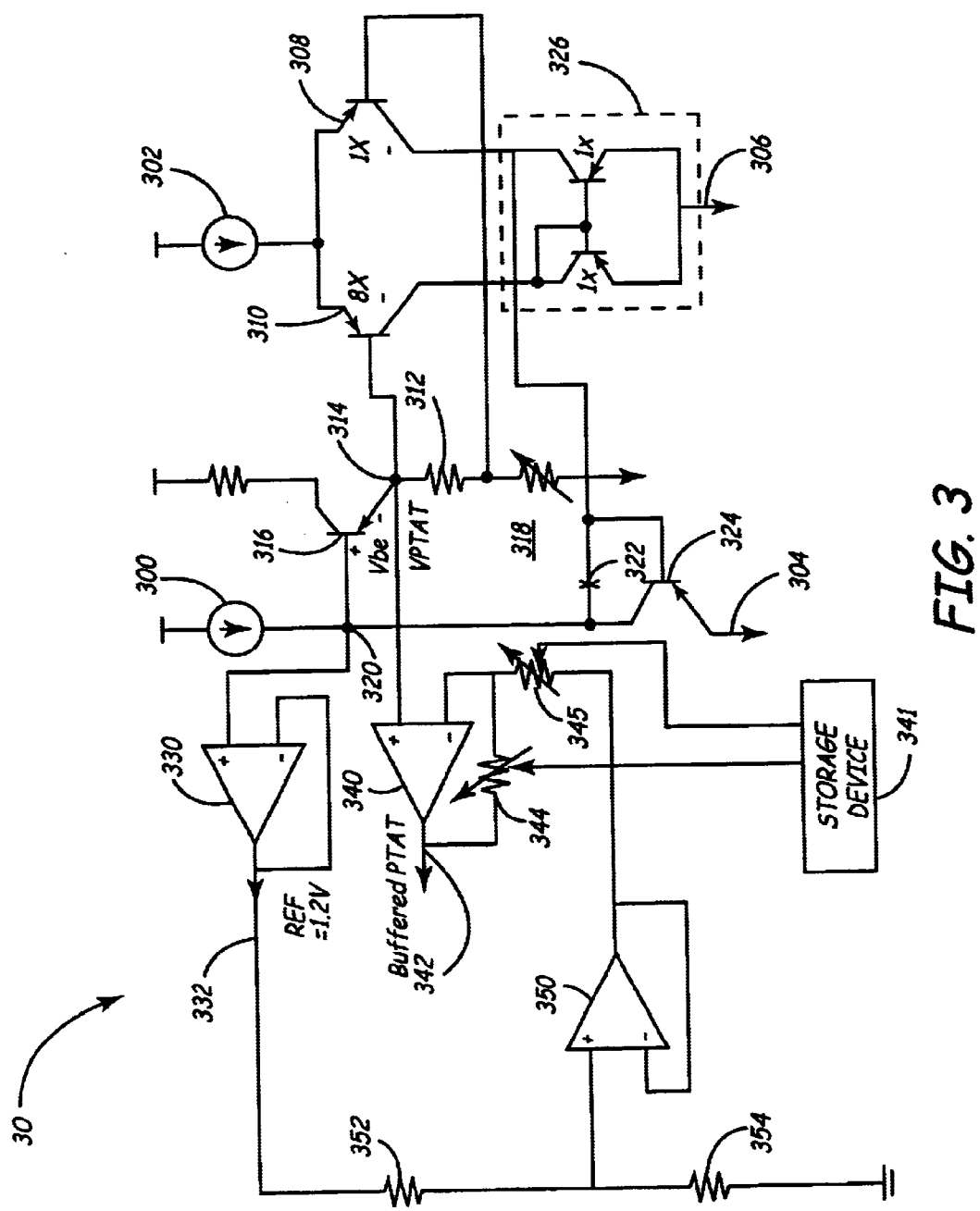
FIG. 3 is circuit schematic of a temperature sensor circuit that may be used by an IMD.

FIG. 3 is a circuit diagram of an exemplary temperature sensor as may be used in the present invention. This type of sensor is referred to as a "Proportional to the Absolute Temperature" (PTAT) temperature sensor circuit. Although this type of circuit is shown and described as temperature sensor 30, it will be appreciated that any other type of temperature sensor that may be adapted for use within an IMD may be substituted for the circuit of FIG. 3 in the current invention. For example, the temperature sensor may utilize a thermocouple as disclosed in U.S. Pat. No. 5,596,995 to Sherman et al., incorporated herein by reference in its entirety. Alternatively, the temperature sensor may use a thermistor, as discussed in U.S. Pat. No. 5,509,424 to Al-Ali, also incorporated herein by reference in its entirety. Other types of temperature sensors are known in the art, and may be employed in place of the PTAT temperature sensor discussed below.

Temperature sensor 30 includes current sources 300 and 302 that are electrically connected to a battery 230 (not shown in FIG. 3) through a regulator such as regulator 200e. Regulator provides a regulated voltage, preferably on the order of two volts, to the temperature sensor circuit 30. Temperature sensor circuit 30 is connected to the negative terminals of battery 230 at electrical connections 304 and 306.

Current from current source 302 is divided equally between transistors 308 and 310. Transistors 308 and 310 and all the devices in the circuit are preferably bipolar transistors although MOSFET transistors having greater process variations and electronic noise could also be used. Transistors 310 and 308 are mismatched at a predetermined ratio, which may be eight to one, although other ratios may be used. When an eight-to-one ratio is used, the emitter area of transistor 310 is eight times the emitter area of a connected transistor 308. Current mirror 326 maintains the collector current in transistors 308 and 310 to be substantially equal to each other and to the emitter current. The difference in the output voltage at the base of transistor 310 and at the base of transistor 308 is applied across resistor 312 to yield a voltage that is proportional to absolute temperature (VPTAT) through the equation:

$$VPTAT \frac{nk}{q} T \ln(8)$$

where n is a device characteristic or parameter constant, k is Boltzmann's constant, T is the temperature in degrees Kelvin, q is the charge of an electron, and ln(8) is the natural logarithm of eight, which in this case is the ratio of the size of transistor 310 to that of transistor 308. This value will vary if another ratio is selected for mismatched transistors 308 and 310. All parameters, except temperature, are constants. Thus, the difference between the base voltage of transistor 308 and base voltage of transistor 310 as applied across resistor 312 is a voltage proportional to the absolute temperature of the PTAT circuit.

The voltage difference across the base-emitter of transistor 316 is proportional to voltage at node 314, which is the same as the voltage across resistor 312. Thus the voltage gain can be determined by setting the ratio of resistor 312 to variable resistor 318. Resistor 318 is used to fine tune the circuit and need only have a limited range to compensate for the slight deviations of the other components from ideal values because of manufacturing process variations. Node 314 is connected to the positive input of the negative feedback amplifier 340, therefore the voltage difference across transistors 308 and 310 is given by:

$$V = \left(\frac{R_{318} + R_{312}}{R_{312}}\right)\left(\frac{nk}{q}\right) T \ln(8)$$

In this equation, $R_{312}$ and $R_{318}$ are the values of resistors 312 and 318 respectively. As mentioned, the voltage V is applied to negative feedback amplifier 340 to provide an analog voltage output 342 that is proportional to the absolute temperature of the IMD 10. This output voltage is provided to ADC 200k to be converted to a digital format, and to other circuitry shown in FIG. 2. This will be discussed further below.

A second negative feedback amplifier 350 having a preferred input voltage on the order of 0.8 volts is connected through variable resistors 344 and 346 to the negative input of amplifier 340 to set the gain of amplifier 340 as is known in the art. This gain may be varied by programmably altering the values selected for these resistors. That is, in the preferred embodiment, microprocessor 250 is capable of storing programmable values in storage device 341 to re-select the values of resistors 344 and 346, thereby changing the gain of amplifier 340. In a default setting, the gain of amplifier 340 is set so that a wide range of temperatures may be detected. This gain may be re-programmed so that a much more narrow range of temperatures may be detected with a greater degree of accuracy. This may be desirable if the temperature is found to be within a particular range of interest, such as near body temperature. Re-programming of the gain is discussed in more detail below.

Returning to FIG. 3, bandgap amplifier 330 provides a reference bandgap voltage 332 that is stable with respect to temperature. This temperature-independent voltage is generated by summing a voltage having a negative temperature coefficient with a voltage having a positive temperature as follows The base-emitter junction of bipolar transistor 316 generates the voltage having a negative temperature coefficient. The difference of the base-emitter voltage between the two mismatched transistors 308 and 310 generates a voltage with a positive temperature coefficient. These two voltages are summed at node 320 and are provided to the positive terminal of amplifier 330. Transistor 324 is an output device that drives the bandgap node 320. Capacitor 322 adds a dominant pole and stabilizes the circuit from oscillation. This bandgap voltage 332 can be provided to other circuit devices shown in FIG. 2.

Figure 4A:
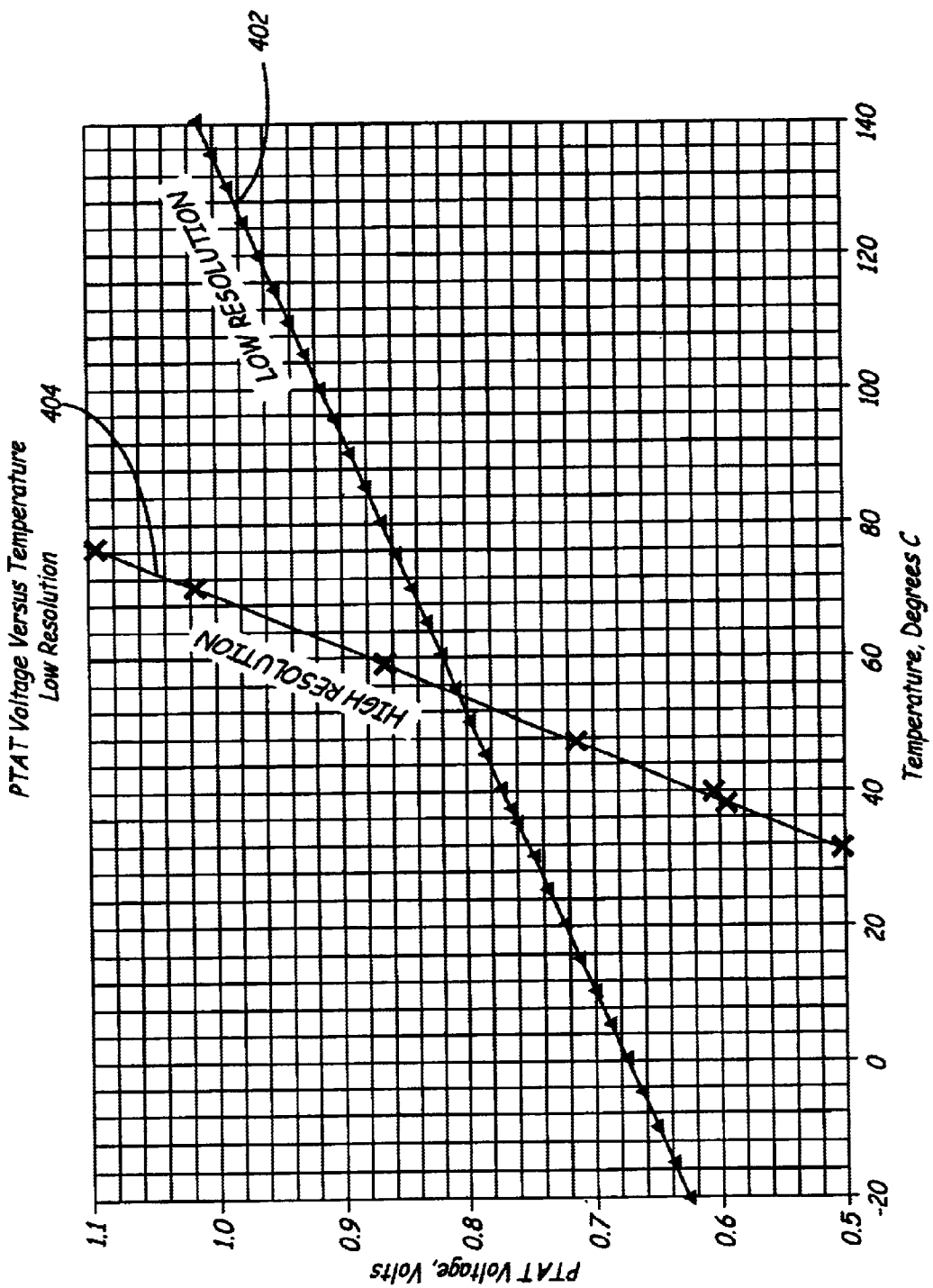
FIG. 4A is a graph of the high range/low sensitivity analog output of the temperature sensor.

FIG. 4A is a graph of the analog voltage output from the temperature sensor 30 as a function of temperature. This graph includes two sets of data. The first set, illustrated by waveform 402, represents the transfer function of the temperature sensor with the gain of amplifier 340 illustrated in FIG. 3 set to a default value. This gain setting allows ADC 200k to provide a digital representation of the temperature over a relatively wide range of temperatures extending from −20° C. to 140° C. This range includes any possible high temperatures occurring during burn-in as well as possible low temperatures that may occur during storage of the IMD 10 in cold-weather temperate zones.

As discussed above, in the preferred embodiment, microprocessor 250 may re-program the gain of amplifier 340 when a temperature reading of particular interest is measured. For example, if a succession of temperature readings around body temperature are detected, the microprocessor may re-program the gain of amplifier 340 so that ADC 200k is able to provide a much more precise digital representation of a temperature measurement over a smaller range of temperatures. This is shown by waveform 404. In one embodiment, the gain of amplifier could automatically be re-programmed by microprocessor 250 upon detection of implant.

Figure 4B:
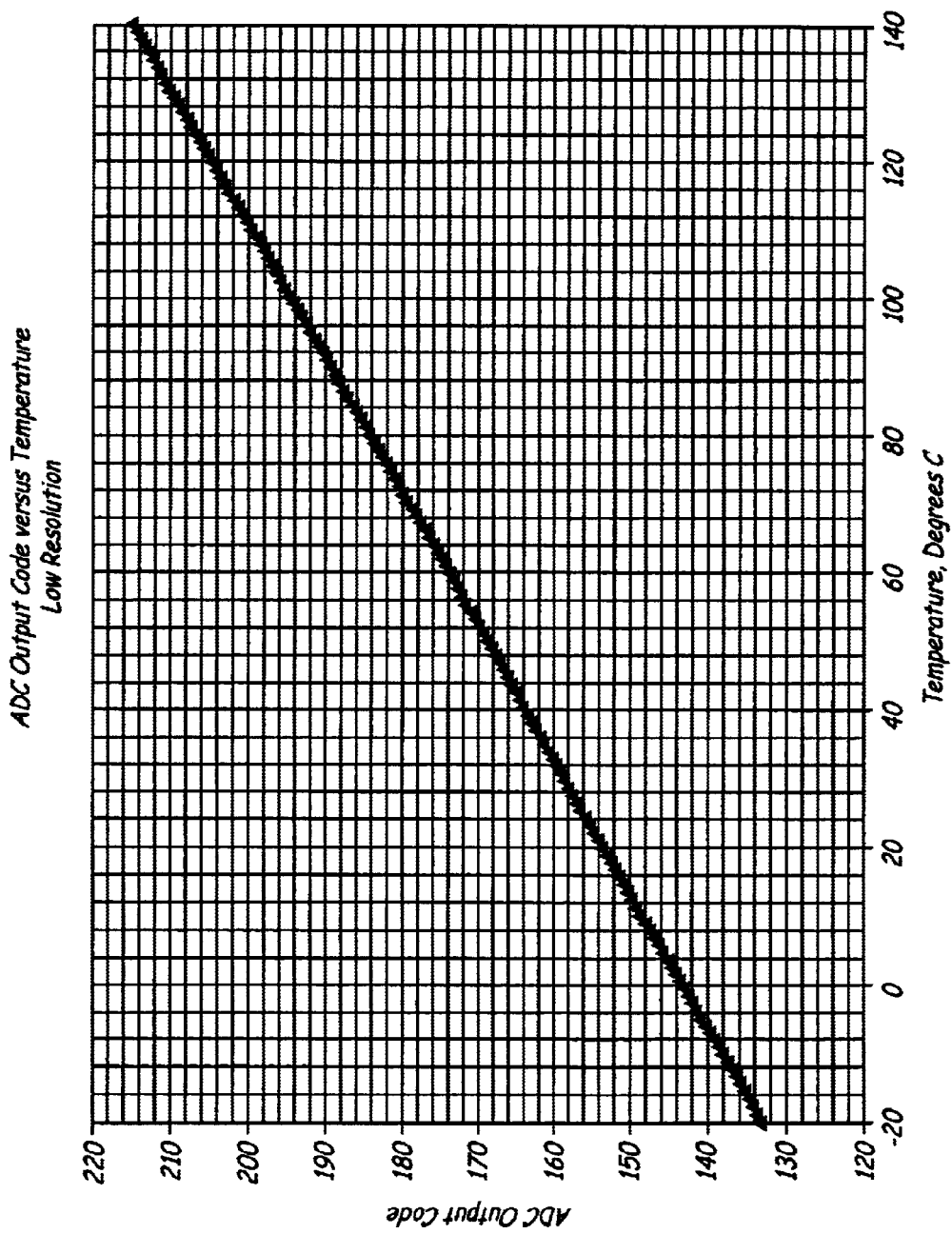
FIG. 4B is a graph illustrating exemplary digital codes provided by an Analog-to-Digital converter as a function of temperature when the temperature sensor is operating in low-resolution mode.

FIG. 4B is a graph illustrating exemplary digital codes provided by the ADC 200k as a function of temperature when the temperature sensor is programmed to operate in low-resolution mode.

Figure 4C:
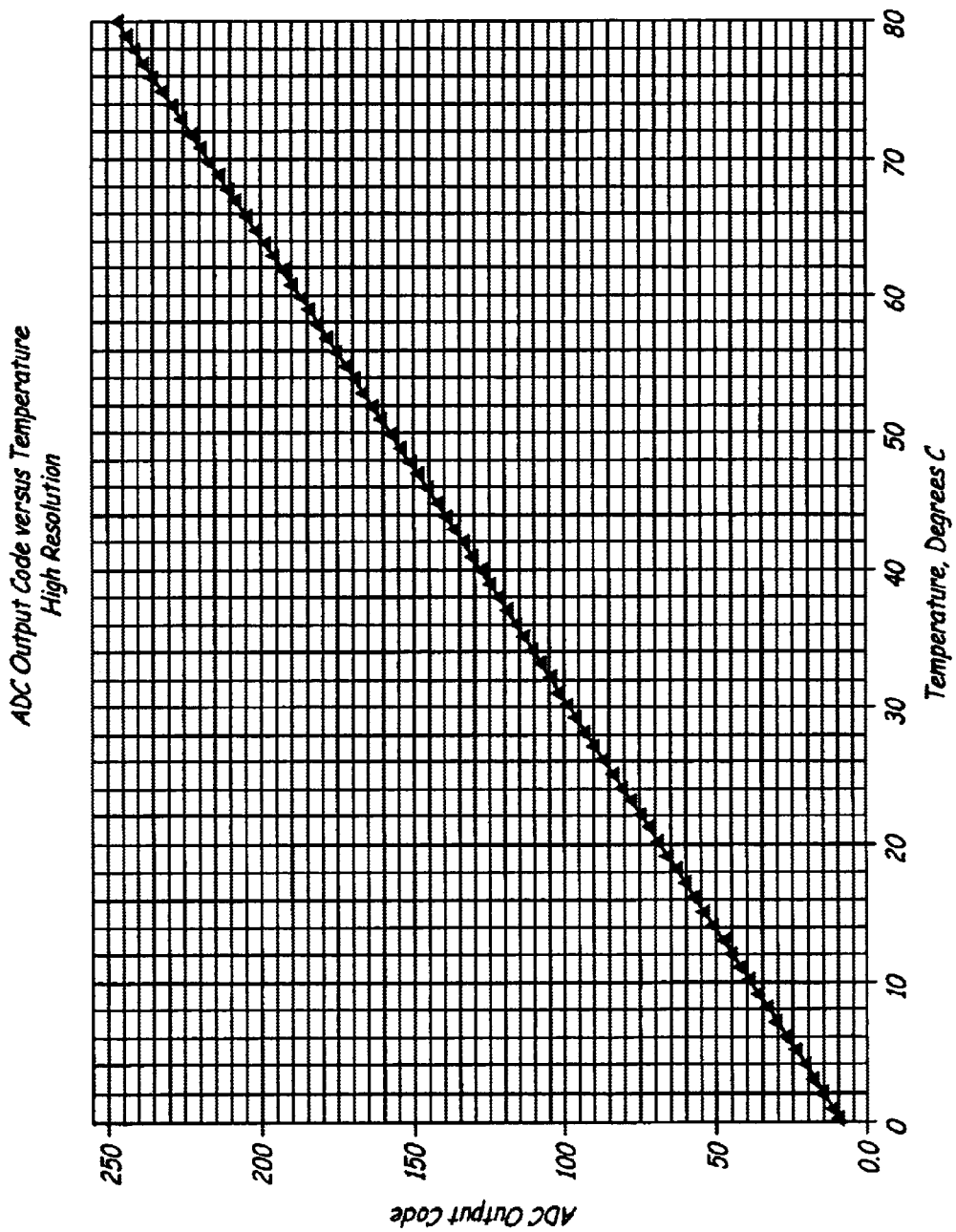
FIG. 4C is a graph illustrating exemplary digital codes provided by an Analog-to-Digital converter as a function of temperature when the temperature sensor is operating in high-resolution mode.

FIG. 4C is a graph illustrating the exemplary digital codes provided by the ADC 200k as a function of temperature when the temperature sensor is programmed to operate in high-resolution mode.

The codes shown in FIGS. 4B and 4C may be processed by a digital processing circuit according to any of the methods discussed below. It will be understood that the transfer functions illustrated by the waveforms of FIGS. 4A through 4C are by way of example only, and are not intended to be limiting. Different transfer functions may be achieved by selecting alternative component values for the PTAT temperature sensor, or by utilizing a different type of temperature sensor altogether as discussed above.

C. Using Temperature to Control Logic Functions of an IMD

Figure 5:
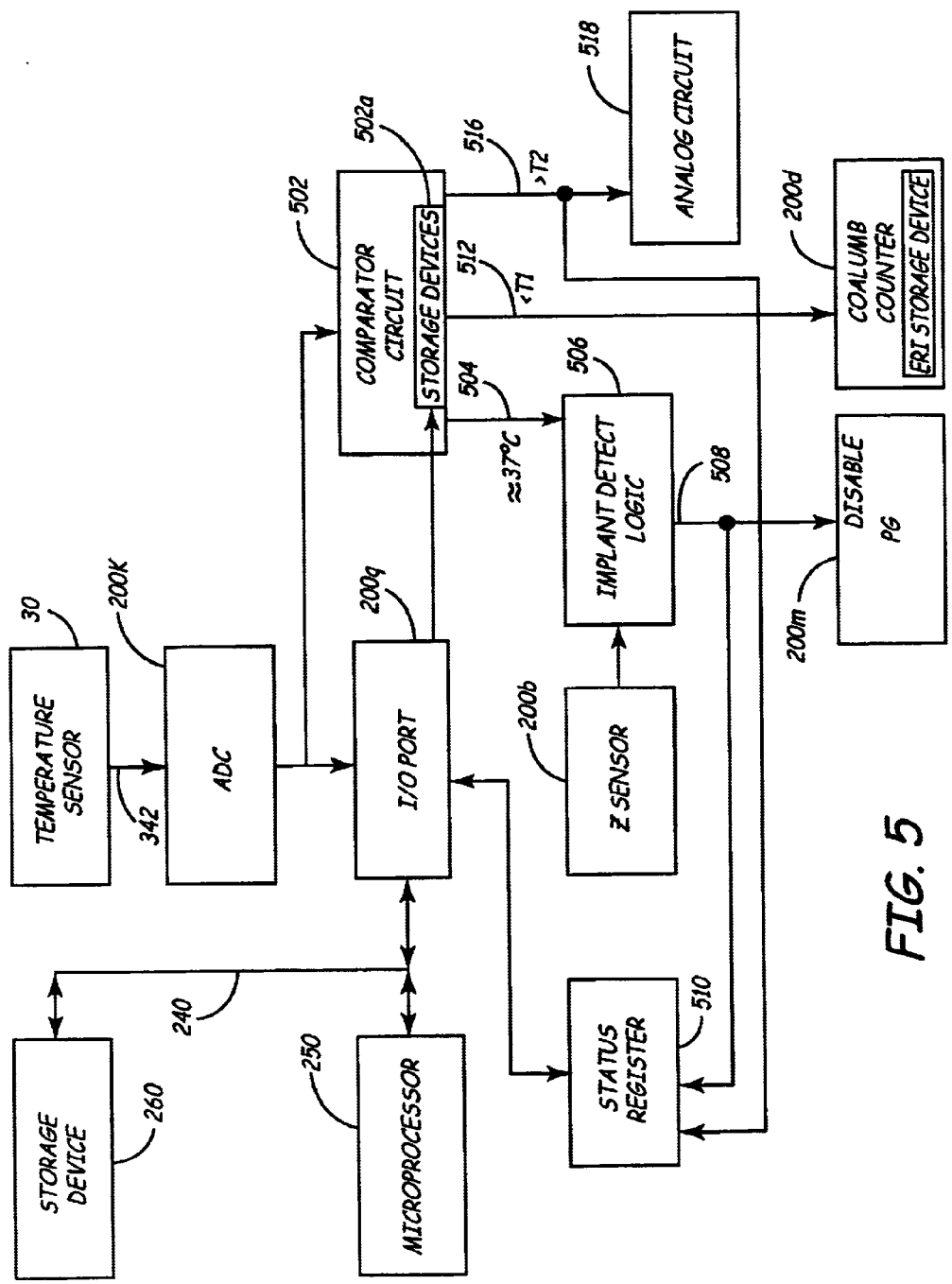
FIG. 5 is a logic block diagram illustrating one embodiment of a system utilizing temperature measurements to control the logical functions of the IMD.

FIG. 5 is a logic block diagram illustrating one embodiment of a system utilizing temperature measurements to control the functions of the IMD. In this embodiment, temperature sensor 30 provides analog temperature measurements to the ADC 200k on line 324 as shown in FIG. 3. These analog temperature measurements are converted by ADC 200k to digital format, and may be stored in storage device 260 via I/O port 200q and bus 240. These digital temperature measurements may also be provided to a comparator circuit 502. Comparator circuit 502 generates control signals to modify the operation of the IMD. For example, a signal shown on line 504 may be generated when the temperature is approximately body temperature, or 37° C. This signal is provided to implant detect logic 506, which determines whether implant has occurred. Implant detection could be determined, for example, by the detection of a temperature that approximates body temperature and that persists for a predetermined number of clock cycles. Alternatively, the body-temperature measurement could be used in conjunction with information such as an impedance measurement provided by impedance sensor 200b, or a measurement from a motion detector such as accelerometer 210 to determine that implant has occurred.

Implant detect logic 506 provides an implant detection signal on line 508 to various functional logic groups within the IMD. This signal could be used, for example, to disable the pulse generator 200m and other logic functions when implant has not yet occurred so that battery power is preserved. The detection of an implant signal could also be latched in a storage device such as status register 510 that is readable by the microprocessor 250 via I/O port 200a. The implant detection signal could then be interrogated by the microprocessor to determine whether certain diagnostic routines should be executed. For example, it may be desirable to disable the execution of some diagnostic routines prior to implant to conserve battery power.

Comparator circuit 502 could also provide other signals for controlling the functionality of the IMD. As discussed above, an IMD subjected to cold temperatures prior to implant will experience a drop in battery voltage and current. This voltage drop, or the voltage increase that occurs upon subsequent re-warming of the IMD, may cause the erroneous latching of the ERI indicator. This may, in turn, cause the IMD to enter a power-saving mode that can only be exited via a manual override procedure. To prevent this from occurring so that the IMD remains in a fully-functioning state, a signal on line 512 could be asserted when the temperature is below a predetermined temperature T1. This signal could .be provided,.for example, to coulumb counter 200d to disable the latching of the ERI indicator within ERI storage device 514.

Comparator circuit 502 may also generate a signal on line 516 when temperature measurements exceed a second predetermined temperature T2. This signal could be provided to certain analog circuitry shown in block 518 to enable a compensation that could, for example, provide additional current to ones of the analog circuit functions. This would allow this circuitry to continue to operate normally at high temperatures.

In one embodiment, comparator circuit 502 could include storage devices 502a to receive programmable data either from an external programmer or via microprocessor 250 and I/O port 200q to select temperatures T1 and T2.

Figure 6:
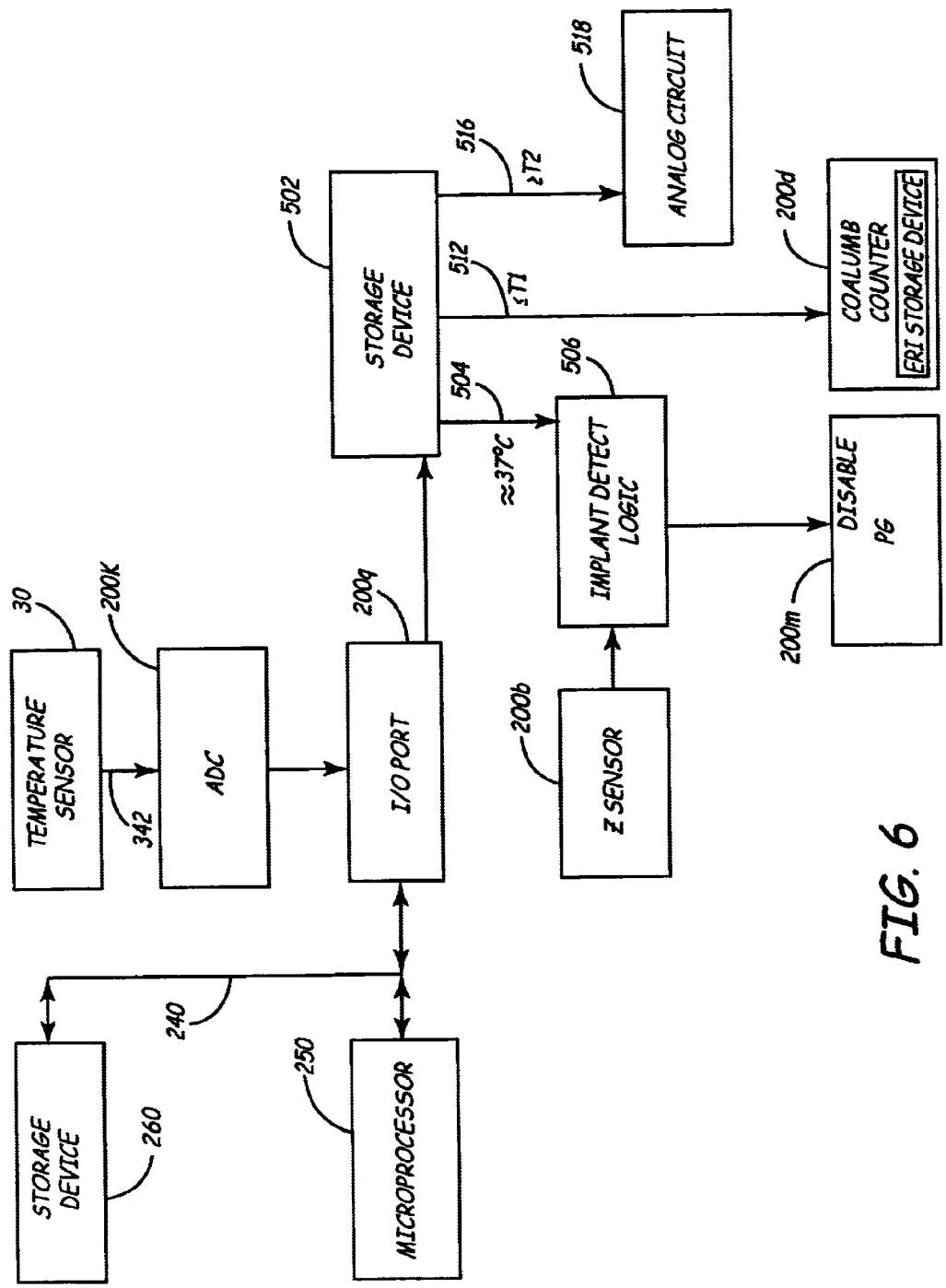
FIG. 6 is a logic block diagram of an alternative embodiment of a system utilizing temperature measurements to control the logical functions of the IMD.

FIG. 6 is a logic block diagram of an alternative embodiment of a system utilizing temperature measurements-to control the logical functions of the IMD. In this embodiment, digitized temperature measurements are provided by ADC 200k via I/O port 200q to storage device 260. These measurements are available to microprocessor 250, which determines whether the temperature has reached one of the predetermined temperatures of interest. In response, microprocessor 250 programs indicators in storage device 520 via I/O port 200q. These programmable indicators assert the various signals shown on lines 504, 512, and 516, which operate to control the logic functions of the IMD in a manner similar to that discussed above with respect to FIG. 5.

It may be noted that temperature and timer measurements stored in storage device 260 may also be utilized for diagnostic purposes. For example, these measurements may be provided to an external programmer via a telemetry link along with any other stored information. This information may be useful in interpreting other cardiac signals stored by the IMD, for diagnosing a patient illness, or for establishing trend data indicative of a changing health condition. The temperature measurements may also be used by microprocessor 250 to adjust various pacing parameters stored by the PG 200m and that control the pacing function. For instance, it may be desirable to detect a temperature that is a predetermined amount above body temperature, and in response thereto, to limit the upper pacing limit until the temperature decreases. This would provide an upper pacing rate during periods of prolonged exercise. Similarly, a prolonged elevation in temperature resulting from exercise may be used to adjust the pacing decay rate following a long period of exercise. For example, it is often desirable to slow the pacing rate more gradually from an elevated pacing rate to a normal pacing rate following a period of extended activity. It may be noted that an accelerometer 210 or other motion sensor may be used in conjunction with the temperature measurements to confirm the occurrence of exercise. Temperature measurements could also be used to set a fixed lower pacing limit. This may be desirable if a predetermined drop in temperature is detected, as may occur during ice baths or similar medical treatments. This prevents pacing from dropping to an excessively low rate that may result in a slowing of the metabolism.

Figure 7:
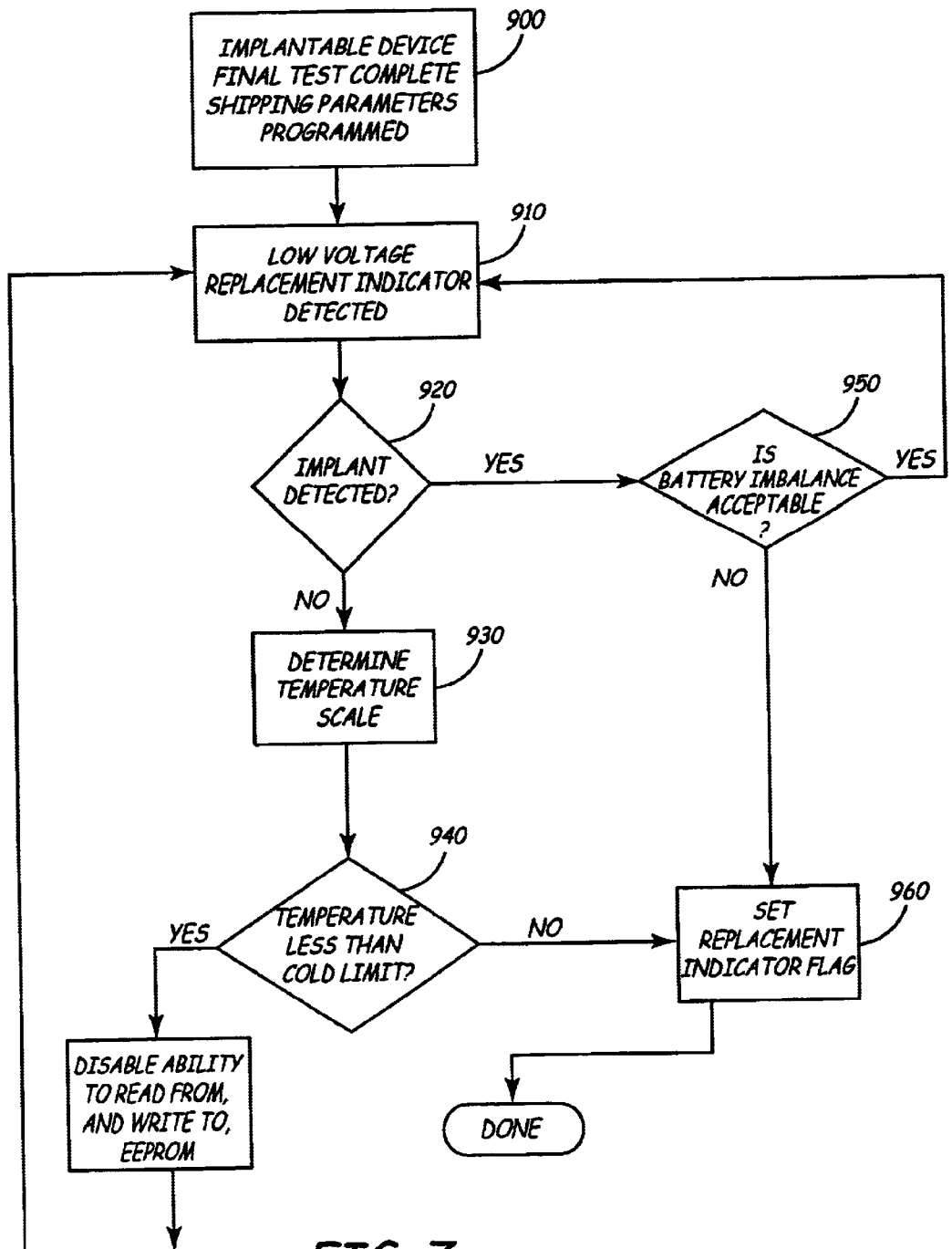
FIG. 7 is a flow chart of a method using the temperature sensor circuit 30 to detect whether the low voltage output of a battery is the result of cold storage temperatures or is a true ERI indicator.

FIG. 7 is a flow chart of one method that may be used with the temperature sensor circuit 30 to detect whether the low voltage output of a battery is the result of cold storage temperatures or is a true ERI indicator. In step 900, the IMD 10 has been tested and is determined to function properly. The IMD 10 is programmed to a quiescent mode as may be accomplished by storing parameters in a memory such as EEPROM 220 of the pacemaker electronic circuitry 200 shown in FIG. 2. In step 910, low voltage and low current from the battery 230 is detected by the battery interface 200*t* and coulomb counter 200*d* which triggers a query to determine if the pacemaker has been implanted in step 920. Implantation of the pacemaker can be independently determined by voltage, current, and impedance measurements output from sense amplifier 200*c* by several techniques, one of which is described in U.S. Pat. No. 5,534,018 entitled "Automatic Lead Recognition for Implantable Medical Device" by Washstand et al which is hereby incorporated by reference in its entirety. As discussed above, implantation can further be confirmed using successive temperature measurements that approximate body temperature.

If implantation is detected, then the microprocessor 250 tests the voltage and impedance of the battery 230 in step 950. If the battery voltage is below a predetermined level and if the impedance of the battery is above a predetermined level then, in step 960, the replacement indicator flag is set.

If an implant is not detected at step 920, then a temperature measurement is taken in step 930. In one embodiment, the measurement process may involve re-programming the gain of amplifier 340 to obtain a higher resolution if the temperature is found to approximate a temperature of interest such as body temperature. This is shown in step 930. If, at step 940, the output of the temperature sensor 30 indicates that a temperature measurement is less than a predetermined temperature such as 0° C. or −18° C., then it is likely that the low voltage reading in step 910 is the result of cold temperature and the output voltage of the battery will increase when the battery 230 is warmed. In this instance, it may also be desirable to disable the ability to read from, and/or write to, the EEPROM, since these functions may not complete successfully at extremely cold temperatures.

If the output of the temperature sensor 30 at step 940 indicates that the battery is not at, or near, the predetermined cold temperature limit, but instead is at a temperature near body temperature, the ERI indicator is set in step 960 to signal that a battery replacement procedure should be scheduled.

Figure 8:
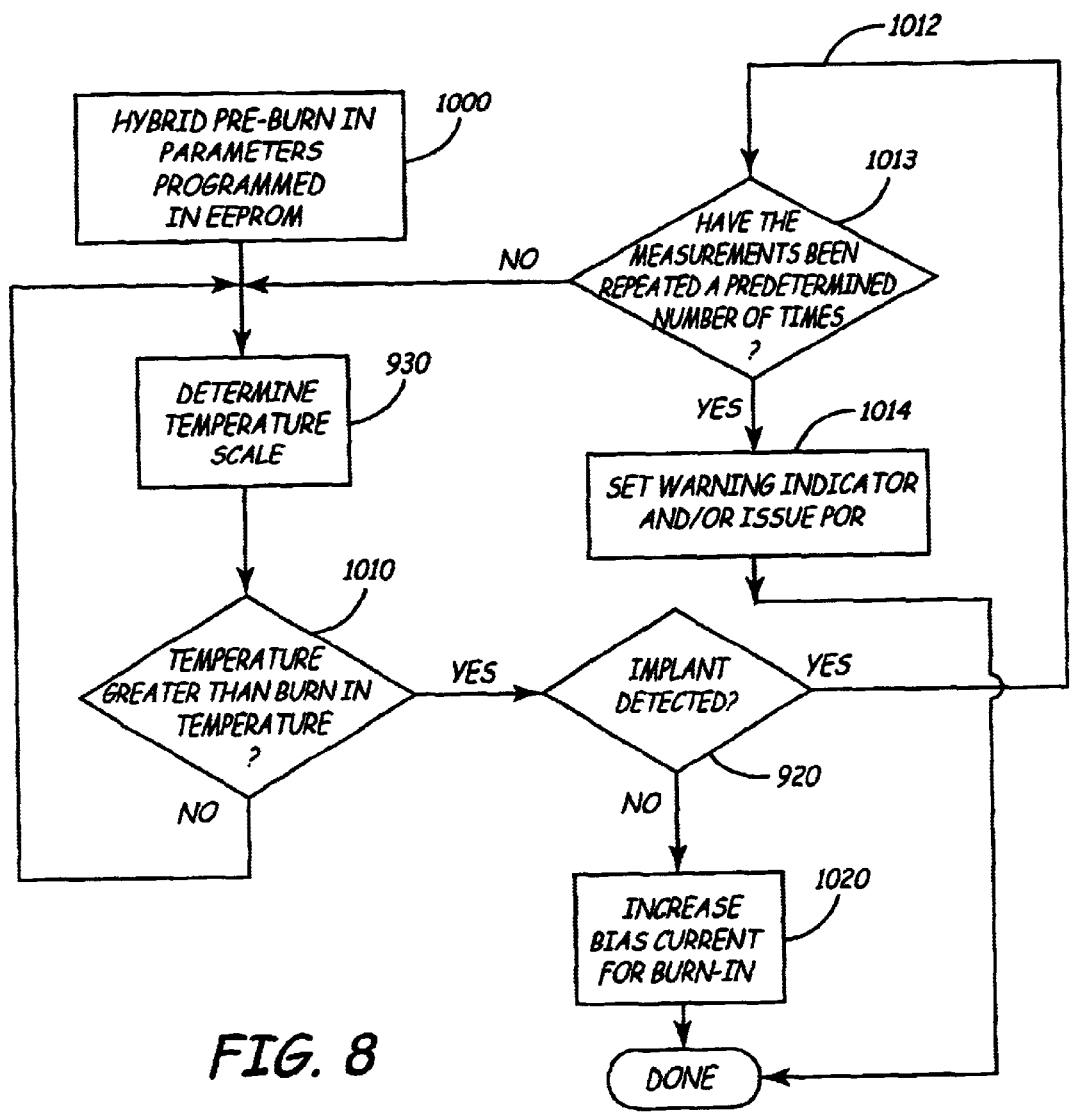
FIG. 8 is a flowchart illustrating a method for using temperature measurements to detect burn-in temperature conditions.

FIG. 8 is a flowchart illustrating one embodiment of a method for using temperature measurements to detect burn-in temperature conditions. In step 1000, burn-in conditions relating to the temperatures, voltages, current strength, and frequencies at which to stress the electronic circuitry of FIG. 2 may be stored in a nonvolatile memory, such as EEPROM 220 and communicated via serial port 200*i*. In step 930, a temperature reading may be taken to automatically determine the scale of the temperature sensor circuit 30. At step 1010, it is determined whether the measured temperature is greater than a pre-programmed burn-in temperature, typically 100 degrees Celsius. If so, the method determines whether the device 10 is implanted within a patient at step 920, using, for example, the method in U.S. Pat. No. 5,534,018 as above. If the device 10 is determined to be implanted, then some circuit malfunction has likely occurred. For example, either the temperature sensor is not functioning properly, or implant has not been detected properly. In one embodiment, the temperature scale could be re-adjusted in step 930 and the process repeated. This is shown by arrow 1012 and block 1013. If the same result is achieved as the measurements have been repeated a predetermined number of times, a warning indicator may be set to indicate the likelihood of-some system malfunction, as shown in block 1014. In this instance, it may also be desirable to mask the ERI indicator since high-temperature operations may cause circuit conditions that result in this indicator being erroneously asserted. In one embodiment, this step could also include issuing a power-on-reset POR signal to reset the electronic circuitry for proper functioning.

If the IMD 10 is found not to be implanted in step 920, then at step 1020, the method may increase the bias current to selected electronic components within the implantable device. Circuits that are sensitive to burn-in conditions such as differential input pairs may be switched to known states. This allows burn-in testing to pass without manual intervention.

Figure 9:
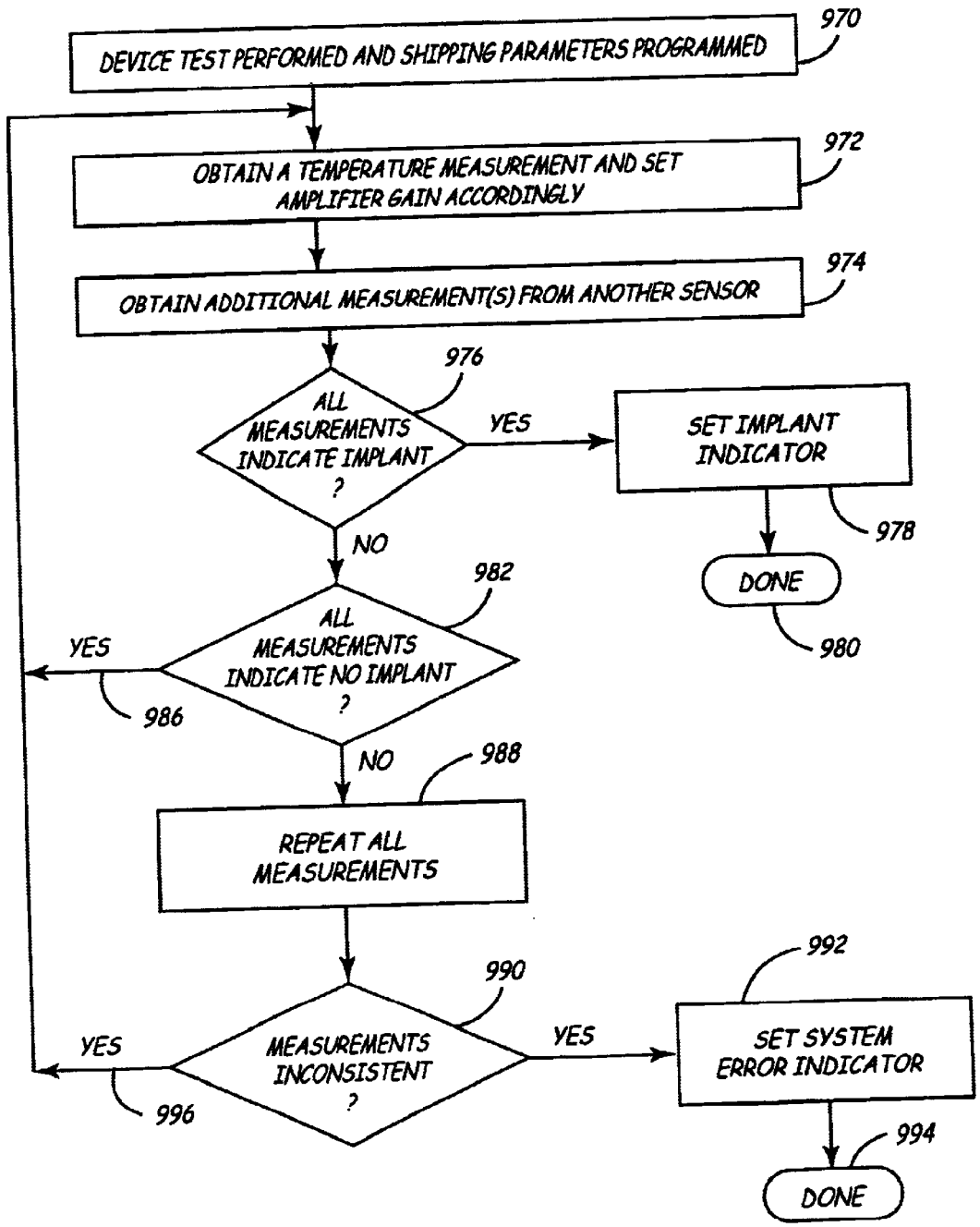
FIG. 9 is a flow chart illustrating a method to detect whether the IMD 10 has been implanted into living tissue.

FIG. 9 is a flow chart illustrating a method to detect whether the IMD 10 has been implanted into living tissue. In step 970, the testing of the IMD 10 has been completed and shipping parameters have been programmed into a storage device such as the EEPROM 220 of FIG. 2. In step 972, a temperature measurement is taken, and the scale of the temperature sensor circuit 30 is adjusted accordingly, if desired. Next, in step 974, another measurement may be taken, if desired, to confirm the temperature measurement. For example, lead impedance measurement may be taken using the impedance sensor 200*b* (FIG. 2) to determine if the lead impedance is indicative of implantation in living tissue. Additionally, or in the alternative, a measurement may be obtained from a motion detector to verify the implantation. If all measurements indicate that implant has occurred in step 976, then in step 978, an indicator is set to indicate that the device 10 has been implanted, and processing is complete as shown in step 980. If the both measurements indicate that implant has not occurred as shown in step 982, processing continues with step 972, as shown by arrow 986 and the process is repeated.

If the various sensor measurements are not consistent, with one measurement indicating implant and another measurement indicating that no implant has occurred, the measurements are repeated, as indicated by step 988. If measurements are still inconsistent, an error indicator is set to indicate a possible system malfunction. For example, a problem may have occurred with one of the sensors. This is shown in steps 990 and 992, respectively. Processing is then complete, as shown in step 994. Otherwise, if the measurements are now consistent, the process may be repeated with additional measurements, as shown by arrow 996.

If desired, the method of FIG. 9 may be adjusted so that implant is determined using only the temperature measurement.

Figure 10:
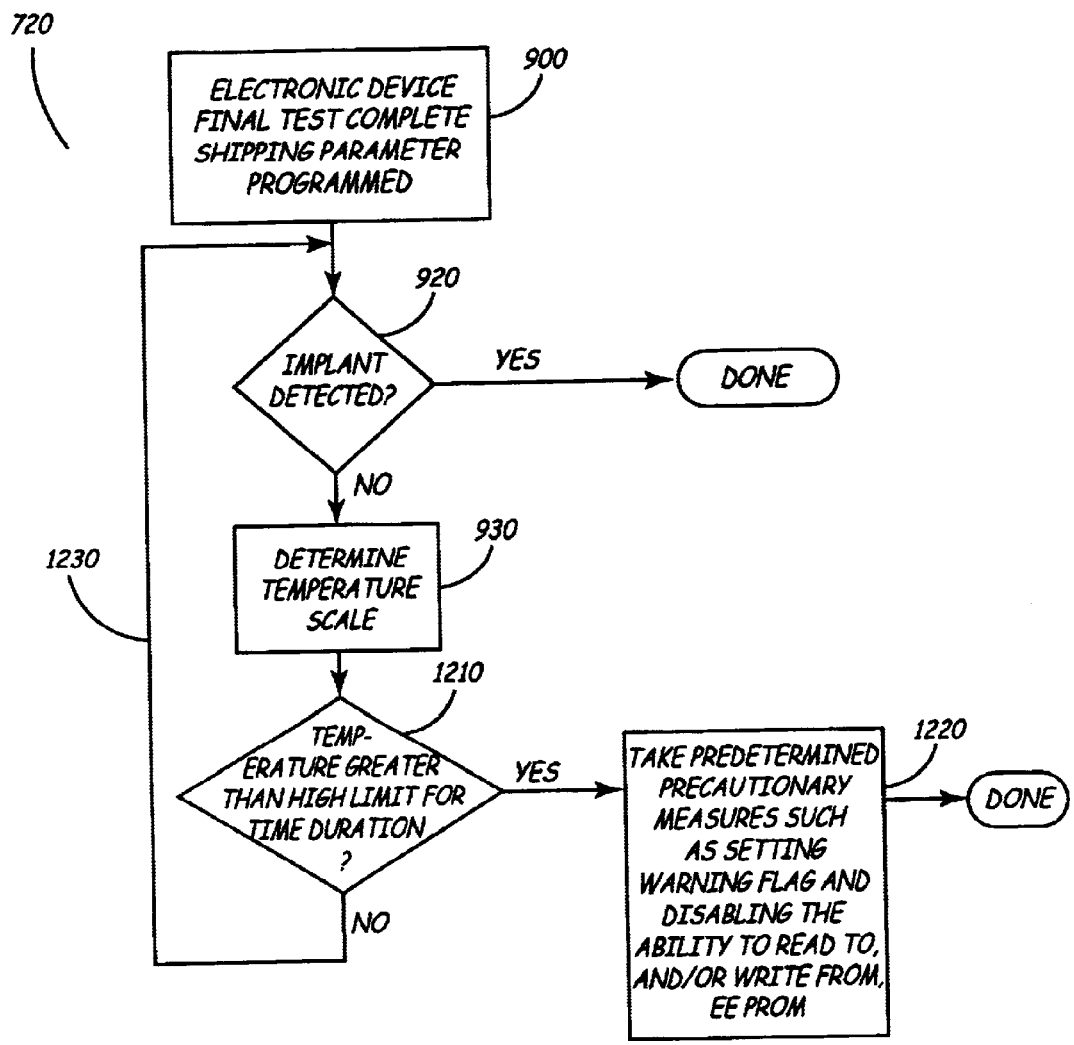
FIG. 10 is a flowchart of a process for using high temperature conditions to initiate the execution of precautionary actions to be taken in response to the IMD being stored in conditions that can compromise the proper functioning of the device.

FIG. 10 is a flowchart of a process for using high temperature conditions to initiate the execution of precautionary actions to be taken in response to the IMD being stored in conditions that can compromise the proper functioning of the device. In response, a warning flag could be set, and/or certain functions can be disabled. In step 900, the IMD 10 is tested and found to be properly functioning and programmed with shipping parameters to minimize power dissipation. In step 920, it is determined whether implant has occurred using one of the mechanisms discussed above. If implantation has occurred, the process is completed. Otherwise, if implantation has not occurred, temperature the appropriate temperature scale is set in step 930 in a manner indicated above.

If the temperature of the IMD 10 is above a high temperature limit for a period of time as detected in step 1210, certain predetermined actions may be taken in step 1220. For example, a warning flag may be set in a storage device of the IMD to indicate that the device should be re-tested prior to implant to verify all systems are operating properly. This flag could be interrogated by a programmer prior to device implant to determine whether the IMD was damaged by heat during the storage period. Other predetermined actions such as disabling certain functions could also be performed in response to the high temperatures. For example, it may be desirable to prohibit either reading from, or writing to, an EEPROM when temperatures are elevated, since these functions may not complete properly at elevated temperatures. Additionally, the ERI indicator may be. masked, since high-temperature operation may cause this flag to set erroneously. If temperatures have not exceeded a predetermined maximum temperature in step 1210, the process may be repeated at a later time interval, as shown by arrow 1230.

Figure 11A:
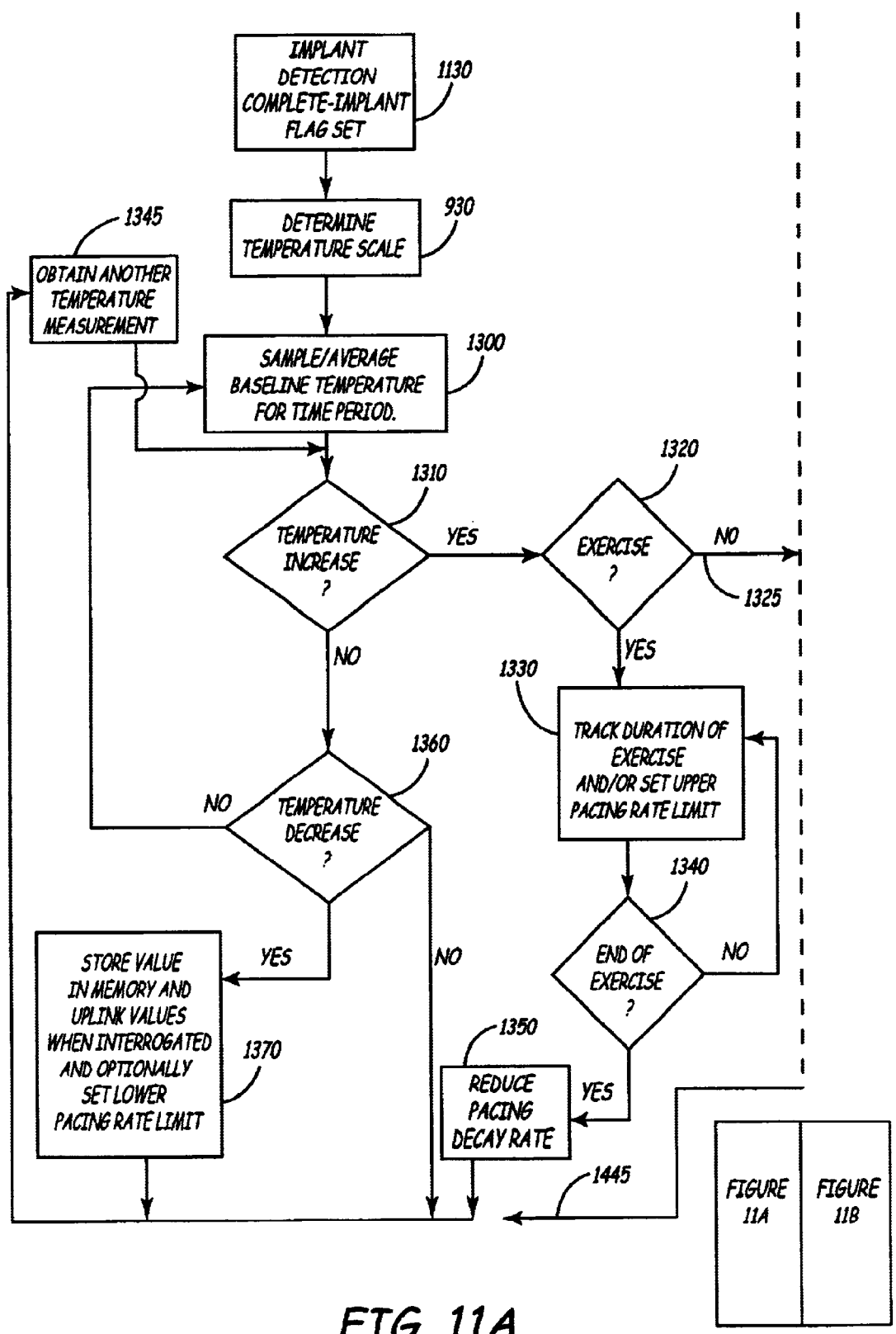
FIGS. 11A and 11B, when arranged as shown in FIG. 11, are a flowchart of a method for using elevated temperatures after implant to provide an independent detection of exercise duration, and to respond by adjusting treatment parameters.
Figure 11B:
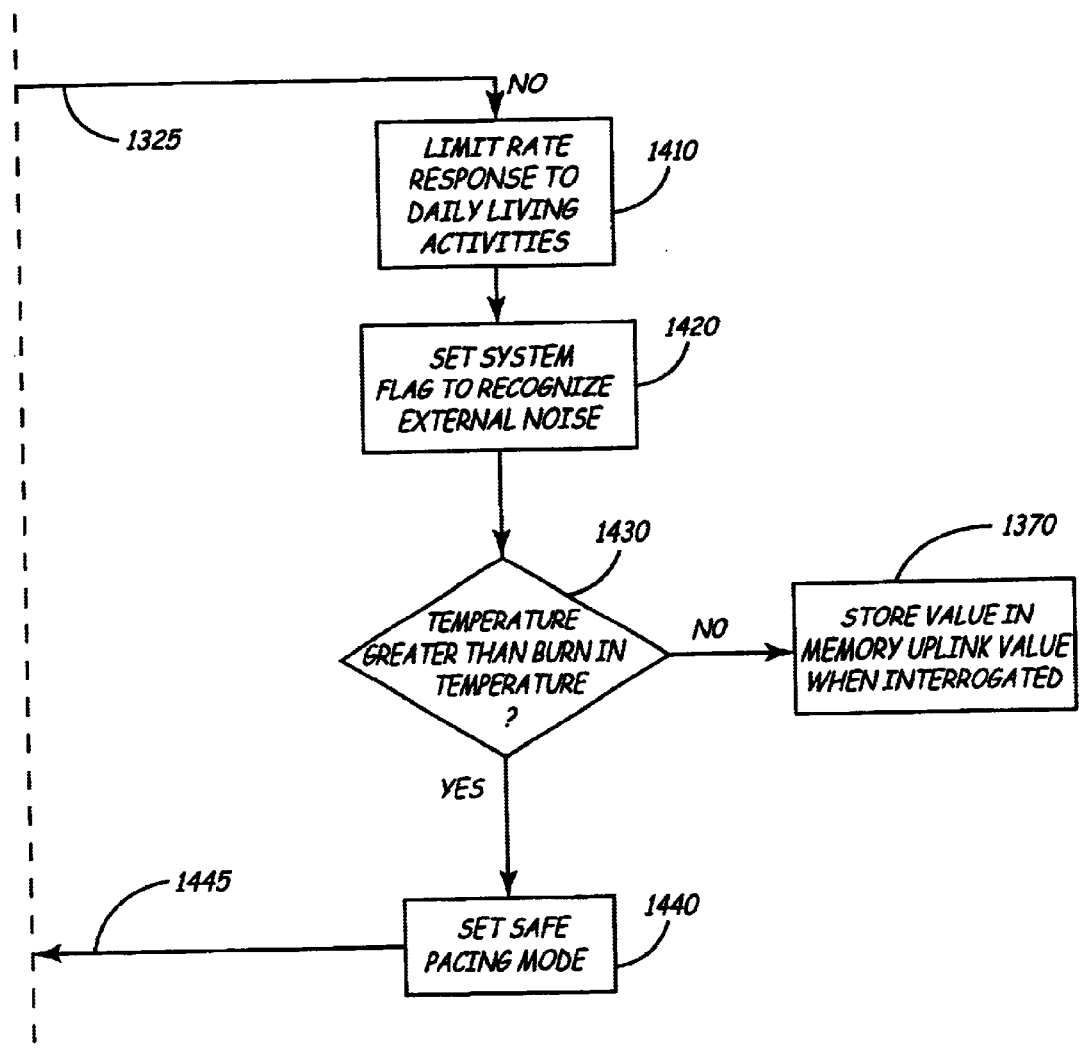

FIGS. 11A and 11B, when arranged as shown in FIG. 11, are a flowchart of a method for using elevated temperatures after implant to provide an independent detection of exercise duration, and to respond by adjusting treatment parameters. In step 1130, proper and complete implantation of the device 10 is established as a prerequisite to invoking the method. If this has been established, the temperature scale is set in step 930, which will generally result in selection of a high-resolution scale within a range of temperatures as may exist in a human body. Next, in step 1300, measurements from the temperature sensor 30 are monitored and stored over a period of time to establish an average baseline temperature of the IMD to indicate the temperature of a patient in whom a pacemaker is implanted. Periodically, if the voltage output of the temperature sensor 30 increases as in step 1310, an inquiry is made in step 1320 to determine if a patient is exercising. This may be accomplished, for example, by evaluating the output of the accelerometer 210 through the accelerometer interface 200h, and/or by using a minute ventilation sensor as described in U.S. Pat. 5,562,711 to Yerich et al. and U.S. Pat. No. 5,052,388 entitled "Method and Apparatus for Implementing Activity Sensing in a Pulse Generator" to Sivula, which is hereby incorporated by reference in its entirety.

If a person is not exercising, processing continues to FIG. 11B, as shown by arrow 1325. In step 1410, pacing rate is limited to a rate appropriate for a non-exercising state as set forth in U.S. Pat. No. 5,562,711 to Yerich et al. A flag indicating the high-temperature condition is set in step 1420. Then in step 1430, the sense amplifier 200c is interrogated to determine if the leads are experiencing measurable noise which may be a result of external radiation such as magnetic resonance interferometry or exposure to x-rays or theft detectors, etc. If the sense amplifier indicates that the leads are experiencing electronic noise, then the IMD 10 can adjust itself to a less demanding mode, as shown in step 1440. For example, if the IMD 10 is a pacemaker, then it may revert to an asynchronous pacing mode, adjust autosensing functions to less sensitivity, or abort the. atrial and ventricular capture managements. This is as described in U.S. Pat. No. 5,713,933 entitled, "Method and Apparatus for Automatic Pacing Threshold Determination" to Condie et al. and U.S. Pat. No. 5,861,013 entitled, "Peak Tracking Capture Detection Circuit and Method" to Peck et al., both of which are hereby incorporated by reference in their entireties. Processing then continues to FIG. 11A, as shown by arrow 1445.

If the sense amplifier 200c does not detect noise in step 1430, the temperature values and trends are stored in memory to be uploaded to a programmer for further diagnosis when the IMD 10 is interrogated. This is shown in step 1370. Processing may then continue to step 1345, as shown by arrow 1445.

Returning now to step 1320 of FIG. 11A, if a patient is exercising, measurements provided by the pulsing timer 200m, an activity sensor, the temperature sensor 30, and other sensors are recorded to track the duration of the exercise in step 1330. At this time, an upper pacing limit may also be established so that the pacing rate does not exceed a predetermined maximum. If exercise has ceased as determined in step 1340, then the pulsing rate of the pacemaker is reduced to a resting rate in proportion to the duration of the elevated temperature using techniques described in, for instance, U.S. Pat. No. 5,052,388 to Sivula et al. This is shown in step 1350. The overall process is then repeated by obtaining another temperature measurement in step 1345, and testing for a temperature increase in step 1310. Otherwise, if exercise continues, the temperature and increased pulsing rate is continuously monitored.

Returning to step 1310 of FIG. 11A, if the temperature does not increase, then in step 1360 the output of the temperature sensor 30 is checked to see if the temperature decreased. If so, the temperature trend and values are stored in memory within microprocessor 250 for further investigation when the data is downloaded through interrogation as in step 1370. This decrease in temperature could also be used to set a lower pacing limit so that the pacing rate does not drop below a predetermined minimum rate. Then another temperature measurement is obtained in step 1345 so that the process may be repeated. If, however, the temperature has not decreased, the process continues in step 1345 by obtaining the next temperature measurement.

The process of FIG. 11 uses measurements provided by temperature sensor 30 to adjust pacing parameters in response to changes in temperature resulting from exposure to external energy sources such as radiation therapy, magnetic resonance diagnostic techniques, diathermy, sonography, or lithotripsy. Such measurements may also be used to adjust therapy during exposure to decreased temperatures such as may occur during ice baths.

Figure 12:
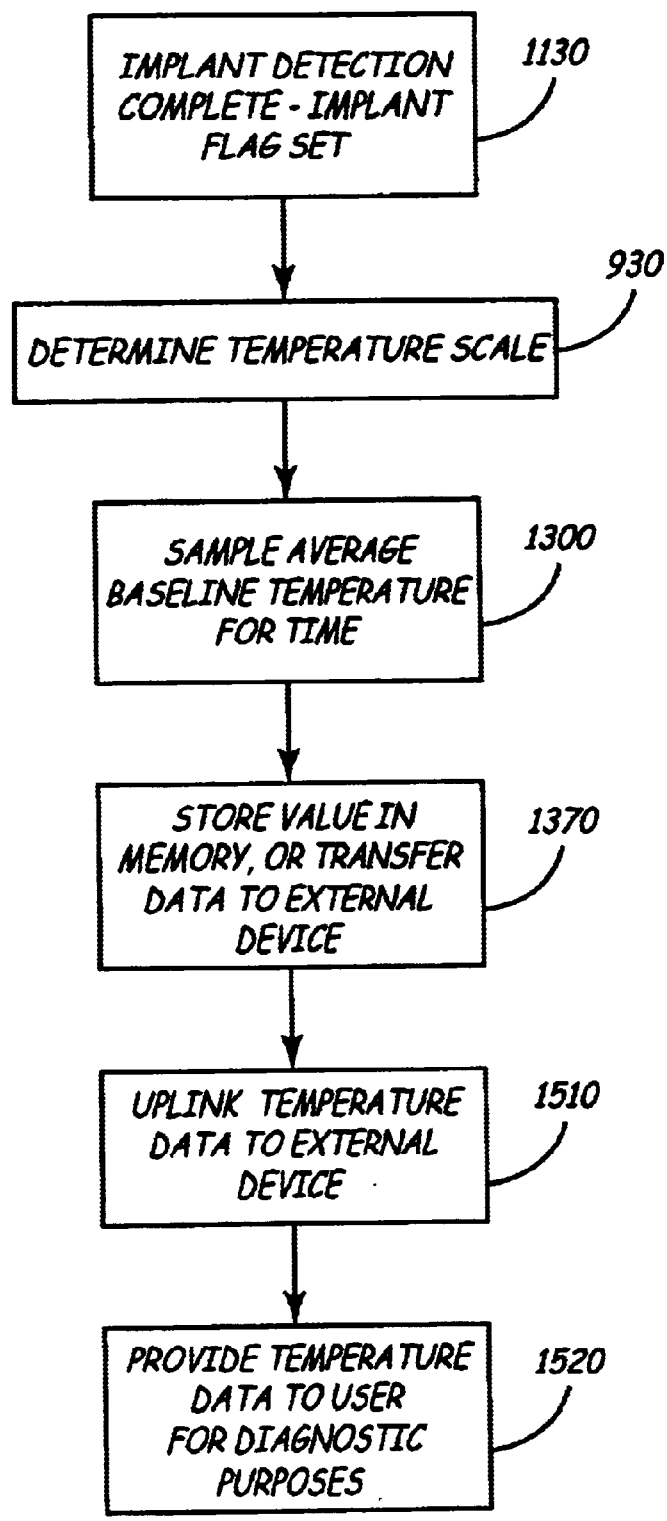
FIG. 12 is a flowchart of a method for storing temperature data measured by the IMD for diagnostic purposes.

FIG. 12 is a flowchart of a method for monitoring temperature, temperature trend data, average and baseline temperatures experienced by the IMD 10. At step 1130, the IMD 10 has been implanted. In step 930, an appropriate temperature scale has been selected. In step 1300, a temperature measurement is taken. Measurements may be stored temporarily in an internal storage device, as shown in step 1370. These measurements may be later transferred to an external device for diagnostic purposes, as shown in steps 1510 and 1520, respectively. As an alternative, temperature data can be transferred in real time to an external device, as shown by arrow 1530.

In yet another embodiment of the invention, temperature measurements may be used to compensate analog functions that are temperature sensitive. For example, some circuits such as Analog-to-Digital Converter (ADC) 200k require a reference voltage to operate properly. However, the reference voltage may drift with temperature changes, causing circuit operation that also varies with the temperature. Voltage compensation circuit 270 (FIG. 2) may be provided to compensate for variations in the temperature. This circuit includes at least one storage device 275 that may be loaded by microprocessor 250. The value that is loaded may be selected based on a current temperature measurement, and causes voltage compensation circuit 270 to compensate for a temperature change so the reference voltage remains relatively constant. This allows the circuit functions of the IMD to remain fairly temperature independent.

Figure 13:
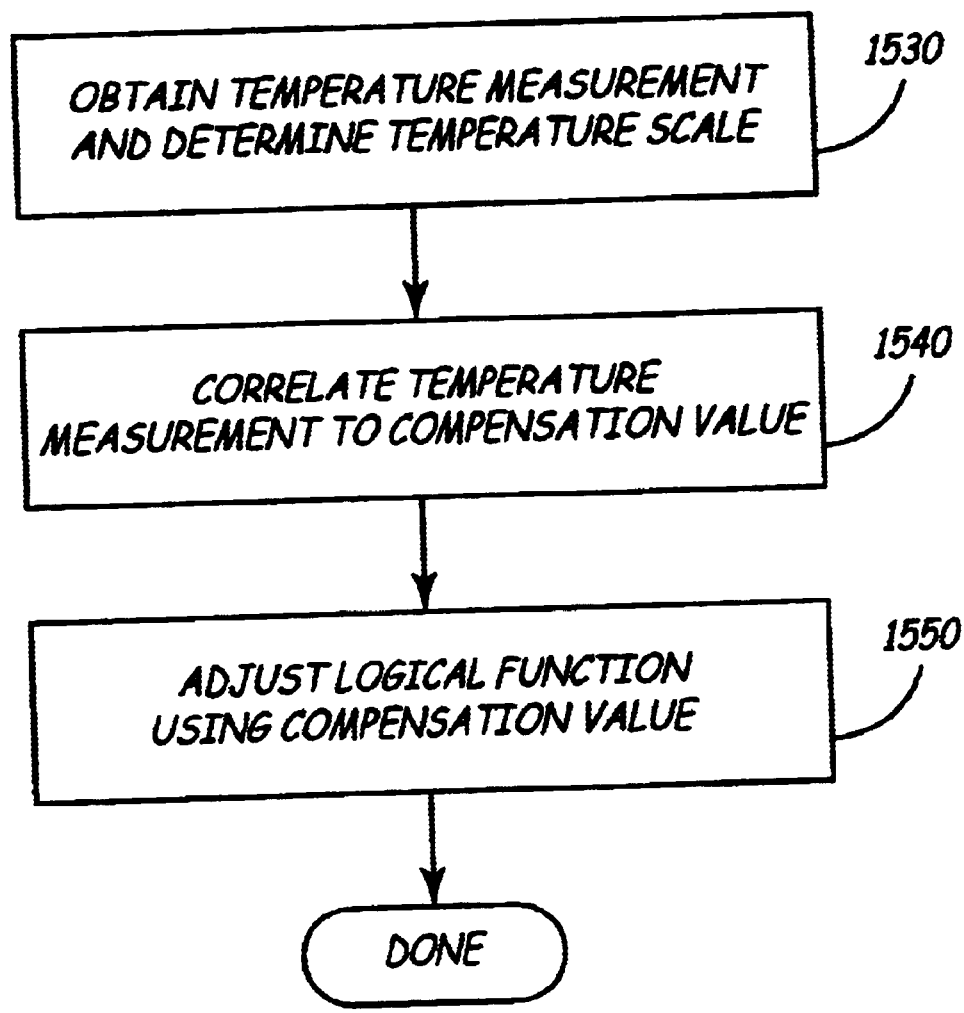
FIG. 13 is a flowchart illustrating a method for compensating a circuit function based on temperature measurements.

FIG. 13 is a flowchart illustrating a method for compensating an analog function based on temperature measurements. In step 1530, a temperature measurement is obtained, and the temperature scale is set in a manner discussed above. In step 1540, the temperature measurement is used to determine a compensation value. In the current example, microprocessor 250 obtains a value that will be used to compensate a temperature-dependent reference voltage, although other types of temperature dependent functions could be compensated using this method. The compensation value could be obtained, for example, using a look-up table stored in a memory of the IMD. The compensation value is then used to adjust the logical function in step 1550, as by being stored in storage device 275. This value may then be used by the voltage compensation circuit 270 (FIG. 2) to adjust the reference voltage in the appropriate manner.

From the foregoing detailed description of a specific embodiment of the invention, it should be apparent that a novel system and method for using temperature measurements to control logical functions of IMDs have been disclosed. Although a specific embodiment of the invention has been described herein in some detail presuming the electronic device is an implantable pacemaker, this has been done solely for the purpose of illustration, and not to limit the scope of the invention. For instance, the device could be a defibrillation system, or a system for implantation to treat conditions unrelated to cardiac disease. Moreover, the scales and resolution set forth are given by way of example only and if the temperature sensor is comprised of semiconductor materials other than bipolar or MOSFETS, such as gallium arsenide or other Group III and Group V compounds, then the range of temperatures and the resolution scale can be adjusted within the IMD 10 accordingly. It is contemplated that various substitutions, alterations and/or modifications to the embodiment of the invention disclosed herein, including but not limited to those implementation options specifically noted herein, may be made to the invention without departing from the spirit and scope of the invention as defined in the appended claims.

What is claimed is:

1. A medical implantable device for delivering therapy to a patient, comprising:
    a therapy delivery unit delivering the therapy to the patient;
    a temperature sensor circuit generating temperature measurements corresponding to the device; and
    a control circuit coupled to the temperature sensor circuit to control system functions of the device other than the delivered therapy in response to the temperature measurements generated by the temperature sensor circuit.

2. The device of claim 1, wherein the control circuit includes means to disable the system functions when the temperature measurements are outside of a predetermined operating range.

3. The device of claim 2, further comprising a battery interface including a battery replacement indicator, wherein the system functions include setting of the battery replacement indicator.

4. The device of claim 1, wherein the control circuit includes means to control the system functions when the temperature measurements are outside of a predetermined operating range.

5. The device of claim 4, further comprising a plurality of sensors generating sensed signals, wherein the means to control the system functions includes means to disable the plurality of sensors.

6. The device of claim 5, wherein the means to control the system functions includes means to adjust voltage or current provided to the plurality of sensors.

7. The device of claim 4, further comprising a storage device storing operation parameters of the implantable device, wherein the system functions include preventing access to the storage device.

8. The device of claim 1, wherein the control circuit includes means to detect when implant has occurred.

9. The device of claim 1, further comprising a plurality of sensors generated sensed signals, wherein the control circuit includes means to indicate when a potential fault has occurred in the generated sensed signals.

10. The device of claim 1, further comprising at least one circuit that is temperature sensitive, wherein the control circuit includes a circuit to calibrate the at least one circuit that is temperature sensitive based on the temperature measurements.

11. The device of claim 1, wherein the control circuit further includes means to control a rate of pulse delivery associated with the delivered therapy.

12. The device of claim 1, and further including a storage device coupled to the control circuit to store the temperature measurements obtained by the temperature sensor circuit.

13. The device of claim 12, wherein the stored temperature measurements obtained by the temperature sensor circuit are further used to diagnose a condition of the patient.

14. The device of claim 1, wherein the control circuit includes means to detect exercise activity of the patient.

15. The device of claim 14, wherein the means to detect exercise activity further includes means to calculate exercise duration.

16. The device of claim 1, and further including a communication circuit coupled to the control circuit to transfer the temperature measurements to a device located external to the medical implantable device.

17. An implantable medical device (IMD), comprising:
    a current supply;
    a temperature sensor circuit sensing a temperature correspond to the implantable medical device, the temperature sensing circuit including two mismatched transistors connected to the current supply, the mismatched transistors having substantially the same collector current and having a voltage difference proportional to the temperature of the IMD;
    a control circuit responsive to the voltage difference to control system functions of the medical implantable device based on the temperature.

18. The IMD of claim 17, wherein the temperature sensor circuit further comprises:
    a resistor, wherein a difference in output voltage at the base of the mismatched transistors is applied across the resistor; and
    an amplifier connected to the resistor to provide an output signal proportional to the temperature to the control circuit.

19. The IMD of claim 17, wherein the mismatched transistors are bipolar transistors having a predetermined ratio.

20. The IMD of claim 19, and further comprising:
    an amplifier device coupled to the mismatched transistors; and
    a gain circuit connected to a negative input of said amplifier device to automatically set a scale and resolution of said temperature sensor circuit.

21. The IMD of claim 18, wherein the amplifier includes a programmable gain programmable to indicate a first range of temperatures with coarse resolution to encompass storage conditions of the IMD, and a second range of temperatures with fine resolution to encompass operating conditions of said IMD.

22. The IMD of claim 21 and further including an analog to-digital converter to provide a digital temperature output of said output voltage proportional to said first and second range of temperatures.

23. The IMD of claim 22, further comprising a plurality of electronic components connected to the analog-to-digital converter wherein said digital temperature output is provided to the electronic components for digital processing and storage, and for monitoring a plurality of functions controlled by the electronic components.

24. The IMD of claim 17, further comprising:

a battery providing power to the implantable medical device; and means for storing information corresponding to available power in the battery and indicating that the available power is at a predetermined value, wherein the control circuit includes circuits to prevent the storing means from indicating that the available power is at the predetermined value when the control circuit determines that the voltage difference indicates the temperature is outside of a predetermined operating temperature range.

25. The IMD of claim 17, and further including a storage device coupled to the control circuit, and wherein the control circuit includes circuits to prevent access to the storage device when the temperature is outside of a predetermined operating temperature range.

26. The IMD of claim 17, and further including a circuit to delivery electrical stimulation to tissue of a patient.

27. The IMD of claim 17, wherein the IMD includes at least one circuit that is temperature sensitive, and wherein the control circuit includes a circuit to calibrate the at least one circuit that is temperature sensitive based on the temperature of the IMD.

28. The device of claim 1, wherein the device is a cardiac pacemaker.

* * * * *